US012642885B2

(12) United States Patent
Raja et al.

(10) Patent No.: US 12,642,885 B2
(45) Date of Patent: Jun. 2, 2026

(54) HEMOSTATIC AND WOUND HEALING TURMERIC-POLYMER COMPOSITE MATERIALS

(71) Applicant: Research Foundation of the City University of New York, New York, NY (US)

(72) Inventors: Krishnaswami S. Raja, Staten Island, NY (US); Andrew Mancuso, Staten Island, NY (US); Christina Viso, West Nyack, NY (US); Kishan Kalluraya Yogesh, Brooklyn, NY (US); Shannon E. Killen, Staten Island, NY (US); Zaghloul Ahmed, Staten Island, NY (US)

(73) Assignee: Research Foundation of the City University of New York, New York, NY (US)

( * ) Notice: Subject to any disclaimer, the term of this patent is extended or adjusted under 35 U.S.C. 154(b) by 219 days.

(21) Appl. No.: 17/939,727

(22) Filed: Sep. 7, 2022

(65) Prior Publication Data

US 2023/0071181 A1     Mar. 9, 2023

Related U.S. Application Data

(60) Provisional application No. 63/241,360, filed on Sep. 7, 2021.

(51) Int. Cl.
| | |
|---|---|
| *A61L 26/00* | (2006.01) |
| *B82Y 5/00* | (2011.01) |
| *B82Y 30/00* | (2011.01) |
| *C08L 67/04* | (2006.01) |

(52) U.S. Cl.
CPC ....... *A61L 26/0019* (2013.01); *A61L 26/0004* (2013.01); *A61L 26/0066* (2013.01); *A61L 26/0076* (2013.01); *A61L 26/0095* (2013.01); *B82Y 5/00* (2013.01); *B82Y 30/00* (2013.01); *C08L 67/04* (2013.01); *A61L 2300/104* (2013.01); *A61L 2300/406* (2013.01); *A61L 2400/12* (2013.01)

(58) Field of Classification Search
CPC ............. A61L 26/0019; A61L 26/0004; A61L 26/0066; A61L 26/0076; A61L 26/0095; A61L 2300/104; A61L 2300/406; A61L 2400/12; A61L 2300/624; A61L 2400/04; B82Y 5/00; B82Y 30/00; C08L 67/04
See application file for complete search history.

(56) References Cited

U.S. PATENT DOCUMENTS

| | | | | |
|---|---|---|---|---|
| 5,401,504 A | * | 3/1995 | Das | ................... A61K 36/9066 |
| | | | | 514/928 |
| 8,383,148 B2 | | 2/2013 | Huey et al. | |
| 8,771,582 B2 | | 7/2014 | Phaneuf et al. | |
| 8,828,050 B2 | | 9/2014 | Gregory et al. | |
| 10,973,946 B1 | | 4/2021 | Hardy et al. | |
| 2011/0104243 A1 | * | 5/2011 | Singhal | .................. A61L 15/40 |
| | | | | 424/446 |
| 2011/0206771 A1 | | 8/2011 | Choi et al. | |
| 2012/0303057 A1 | | 11/2012 | Choy et al. | |

OTHER PUBLICATIONS

Behrens et. al. In Situ Deposition of PLGA Nanofibers via Solution Blow Spinning. ACS Macro Lett. 2014, 3, 249-254 (Year: 2014).*
Kalantari et. al. Wound dressings functionalized with silver nanoparticles: promises and pitfalls. Nanoscale, 2020, 12, 2268-2291. (Year: 2020).*
Sofokleous et. al. Preparation, Characterization, and Release of Amoxicillin from Electrospun Fibrous Wound Dressing Patches. Pharm Res (2013) 30:1926-1938. (Year: 2013).*
He et. al. Effect of Needle Characteristic on Fibrous PEO Produced by Electrospinning. Resolution and Discovery 4(2019)1, pp. 7-11. (Year: 2019).*
Shivalingu et. al. "Comparative analysis of procoagulant and fibrinogenolytic activity of crude protease fractions of turmeric species" Journal of Ethnopharmacology 172 (2015) 261-264. (Year: 2015).*
Dosoky et. al. "Chemical Composition and Biological Activities of Essential Oils of Curcuma Species" Nutrients 2018, 10, 1196. 1-42. (Year: 2018).*
Behrens et. al. (ACS Macro Lett.; 2014)—from previous action (Year: 2014).*
Shivalingu (Journal of Ethnopharmacology, 2015).—from previous action (Year: 2015).*
Sofokleous et. al. (Pharm Res; 2013).—from previous action (Year: 2013).*
Kalantari (Nanoscale, 2020).—from previous action (Year: 2020).*
Kim (2012),—from previous action (Year: 2012).*
Tayyem "Curcumin Content of Turmeric and Curry Powders" (2006) (Year: 2006).*
Sirisidthi "Antithrombotic activity of turmeric (Curcuma longa): A review " Indian J. Agric. Res., 50 (2) 2016 : 101-106 (Year: 2016).*
People's Pharmacy "People's Pharmacy: The medicinal benefits of turmeric" (2011), (Year: 2011).*
Times of India "6 home remedies to heal cuts" (2017). (Year: 2017).*
One Green Planet. "How to Help Heal Cuts and Wounds with Tumeric." (2017) (Year: 2017).*

(Continued)

Primary Examiner — Sean M Basquill
Assistant Examiner — Rajan Pragani
(74) Attorney, Agent, or Firm — Schmeiser, Olsen & Watts LLP; Peter J. Mikesell

(57) ABSTRACT

A method and composite for treating a wound. A wound is sprayed with a composition that includes a volatile organic solvent, a biocompatible polymer and turmeric powder. The solvent evaporates during the spraying. The resulting composite stops bleeding instantly, can remain on the wound for prolonged periods and adheres with the wound, even under arterial pressure. The composite serves to promote wound healing and hemostasis in bleeding wounds.

19 Claims, 3 Drawing Sheets

(56)          References Cited

OTHER PUBLICATIONS

Shivalingu "Comparative analysis of procoagulant and fibrinogenolytic activity of crude protease fractions of turmeric species" Journal of Ethnopharmacology 172 (2015) 261-264. (Year: 2015).*

Behrens "In Situ Deposition of PLGA Nanofibers via Solution Blow Spinning" ACS Macro Lett. 2014, 3, 249-254. (including supporting informaiton) (Year: 2014).*

Sofokleous "Preparation, Characterization, and Release of Amoxicillin from Electrospun Fibrous Wound Dressing Patches" Pharm Res (2013) 30:1926-1938 (Year: 2013).*

Kalantari "Wound dressings functionalized with silver nanoparticles: promises and pitfalls" Nanoscale, 2020, 12, 2268-2291. (Year: 2020).*

Kim, D. et al.; Anticoagulant activities of curcumin and its derivative; BMB Reports; 2012; pp. 221-226; vol. 45 Issue 4; http://dx.doi.org/10.5483/BMBRep.2012.45.4.221.

TELEFLEX; QuikClot® Phamplet; 2021; 2 pages.

XStat —RevMedx Phamplet; 2009; 8 pages.

Nussbaum, N. et al.; An Economic Evaluation of the Impact, Cost, and Medicare Policy Implications of Chronic Nonhealing Wounds; Value in Health; Sep. 19, 2017; pp. 27-32; vol. 21, Issue 1; DOI:https://doi.org/10.1016/j.ival.2017.07.007.

Ulery, B. et al.; Biomedical Applications of Biodegradable Polymers; Polymer Physics; May 5, 2011; pp. 832-864; vol. 49; DOI: 10.1002/polb.22259.

Krausz, A. et al.; Curcumin-encapsulated nanoparticles as innovative antimicrobial and wound healing agent; Nanomedicine: Nanotechnology, Biology and Medicine; Jan. 2015; pp. 195-206; vol. 11, Issue 1.

Eastridge, B. et al.; Death on the battlefield (2001Y2011): Implications for the future of combat casualty care; J Trauma Acute Care Surg; Dec. 2012; pp. s431-s437; doi: 10.1097/TA.0b013e3182755dcc.

Behrens, A. et al.; In Situ Deposition of PLGA Nanofibers via Solution Blow Spinning; ACS Macro Letters; Feb. 26, 2014; 99 249-254; dx.doi.org/10.1021/mz500049x.

Dai, X. et al.; Nano-formulated curcumin accelerates acute wound healing through Dkk-1-mediated fibroblast mobilization and MCP-1-mediated anti-inflammation; NPG Asia Materials; Mar. 31, 2017; 14 pages; doi:10.1038/am.2017.31.

Lim, T. et al.; Poly (lactic-co-glycolic acid) as a controlled release delivery device; J Mater Sci: Mater Med;I Mar. 13, 2009; pp. 1669-1675; vol. 20; DOI 10.1007/s10856-009-3727-z.

Saito, M. et al.; New approaches in tail-bleeding assay in mice: improving an important method for designing new anti-thrombotic agents; Int. J. Exp. Path.; Jul. 5, 2016; pp. 285-292; vol. 97; doi: 10.1111/iep.12182.

Wright, J. et al.; Thermal Injury Resulting from Application of a Granular Mineral Hemostatic Agent; The Journal of TRAUMA Injury, Infection, and Critical Care; Aug. 2004; pp. 224-230; vol. 57; DOI: 10.1097/01.TA.0000105916.30158.06.

Emelike, Nkechi-Juliet Tamuno; Function and Physicochemical Properties of Turmeric Powder as Affected by Processing Methods, Asian Food Science Journal, 19(2) 1-10, 2020, Article No. AFSJ. 62587, Nov. 20, 2020.

Achatya, V. et al.; Modalities of Protein Denaturation and Nature of Denaturants; Int. J. Pharm. Sci. Rev. Res..; Jul.-Aug. 2021; pp. 19-24; 69(2), Article No. 02, http://dx.doi.org/10.47583/ijpsrr.2021. v69i02.002.

Duan, X .et al.; A Straightforward and Highly Efficient Precipitation/On-pellet Digestion Procedure Coupled to a Long Gradient Nano-LC Separation and Orbitrap Mass Spectrometry for Label-free Expression Profiling of the Swine Heart Mitochondrial Proteome; J Proteome Res.; Jun. 2009; pp. 2838-2850; vol. 8 issue 6; doi: 10.1021/pr900001t.

WEBMD; Tumeric, Special Precautions and Warnings; Feb. 26, 2021; 2 pages; https://www.webmd.com/vitamins/ai/ingredientmono-662/turmeric#precautions.

* cited by examiner

HEMOSTATIC AND WOUND HEALING TURMERIC-POLYMER COMPOSITE MATERIALS

CROSS-REFERENCE TO RELATED APPLICATIONS

This application claims priority to, and is a non-provisional of, U.S. provisional patent application 63/241,360 (filed Sep. 7, 2021). The content of this application is hereby incorporated by reference.

BACKGROUND OF THE INVENTION

Annually, the United States reports the cost for wound care to be around $31.7 billion. Hemorrhage is the number one killer on the battlefield for the U.S. army. In the U.S. army, 90.9% of acute mortality was associated with hemorrhage and most soldiers perished before reaching a surgeon. The leading cause of death for people under the age of 46 in the United States is due to trauma and 30 to 40 percent of civilian deaths by traumatic injury are the result of hemorrhage. As mass killing events in the U.S. continue to rise, Hartford Consensus Joint Committee created a policy to increase survival in mass casualty shootings. The policy views stopping hemorrhage as a crucial step to improving the survival of victims of an active shooter. Chronic wounds impact about 15 percent (8.2 million) of Medicare beneficiaries.

Current technologies to address hemorrhage have significant limitations. These include a) making close or direct physical contact with the wound and possible exposure to patient blood, b) ingredients not appropriate for long term use, necessitating removal of the agent from the body, once the victim is transported to a medical facility, c) use of expensive ingredients and lack of availability of ingredients due to supply chain issues, d) ingredients not being biodegradable and bioabsorbable, e) agents appropriate only to arrest hemorrhage but not useful for wound healing, f) possible side effects.

Some technologies which have been used for treating hemorrhage contain zeolite, which promotes blood clotting but has side effects (the reaction of zeolites with blood is exothermic which caused second-degree burns). Other current hemorrhage treatment agents contain kaolin—a white clay. The kaolin-based products are effective in arresting hemorrhage, but the ingredients are not bioresorbable. Other hemorrhage treatment agents are not appropriate for long-term use and need to be removed from the body once the victim is transported to a medical facility. The complications that can arise with these agents include coagulopathy, the development of progressive stages of shock. Added to these issues is the danger associated with the release of fragments of the products into the systemic circulation which can lead to embolus formation. Hence, they are not appropriate for long term use. Still other hemorrhage treatment agents are made from human blood and carry the risk of transmitting infectious agents.

Furthermore, the world is facing several issues that make the treatment of hemorrhage very challenging. These include a global pandemic that overwhelmed the hospital emergency rooms as witnessed during the COVID 19 pandemic, increasing global conflicts, climate change related natural disasters which cause severe delays stretching into several days before a patient can be transported to a medical facility. The issue of addressing hemorrhage in underdeveloped areas of the world that have limited access to medical facilities has been a long-standing issue. The increase in cases of mass shootings in civilian areas where first responder civilians are incapable of administering the treatment due to the fear of coming in contact with the victim's blood and the lack of a readily accessible tools to treat hemorrhage at the point of occurrence are also other urgent matters that need to be solved immediately. An improved technology to address at least some of these issues is therefore desired.

The discussion above is merely provided for general background information and is not intended to be used as an aid in determining the scope of the claimed subject matter.

SUMMARY

This disclosure provides a method and composite for treating a wound. A wound is sprayed with a composition that includes a volatile organic solvent, a biocompatible polymer and turmeric powder. The solvent evaporates during the spraying. The resulting composite stops bleeding instantly, can remain on the wound for prolonged periods and adheres with the wound, even under arterial pressure. The composite serves to promote wound healing and hemostasis in bleeding wounds.

In a first embodiment, a method for treating a wound is provided. The method comprising: spraying a wound with a composition of matter comprising: a volatile organic solvent that at least partially evaporates during the spraying; a biocompatible polymer; turmeric powder; and permitting the volatile organic solvent to evaporate, thereby forming a composite on the wound.

In a second embodiment, a method for forming a composite bandage is provided. The method comprising: spraying a surface with a composition of matter comprising: a volatile organic solvent that at least partially evaporates during the spraying; a biocompatible polymer; turmeric powder; permitting the volatile organic solvent to evaporate, thereby forming a composite on the surface; peeling the composite from the surface, thereby forming the composite bandage.

In a third embodiment, a composite comprising a poly (glycolic acid-lactic acid) and a turmeric powder is provided.

DETAILED DESCRIPTION OF THE INVENTION

Figure 1A:
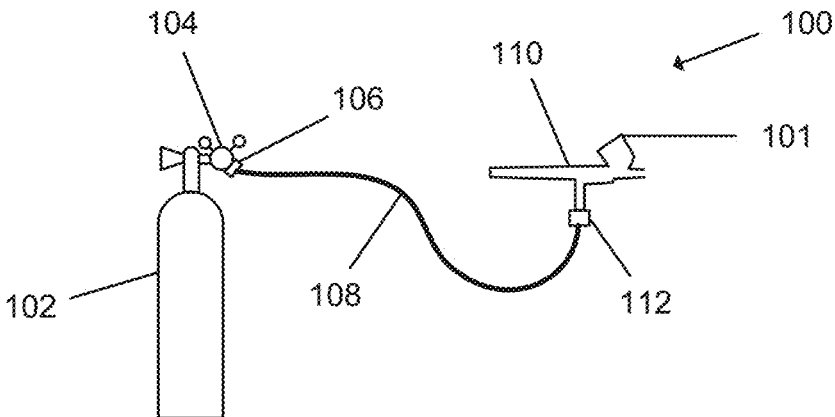
FIG. 1A and FIG. 1B depict two examples of spraying devices useful for deploying the disclosed turmeric powder suspensions.

This disclosure provides a composite of turmeric powder embedded in a biocompatible polymer nanofiber matrix. In one embodiment, the biocompatible polymer is poly (lacticco-glycolic acid), more commonly known as PLGA. In one embodiment, this composite is dispensed from a spraying device powered by a compressed gas. A suspension of the turmeric powder and the biocompatible polymer is formed in a volatile organic solvent (e.g. acetone) and is loaded into the spraying device. When the spraying device is actuated, the suspension is deployed toward a target area. During deployment, the volatile organic solvent evaporates mid-air to produce a composite of turmeric powder and polymer nanofiber matrix that is directly applied to a wound site to arrest hemorrhage and accelerate wound healing. In one embodiment, silver nanoparticles or other antibiotics are present in the suspension.

In another embodiment, bandages are produced by spraying the suspension on a sterile surface and thereafter peeling the resulting polymer nanofiber matrix off the sterile surface. The resulting bandage can be packaged as a roll and later be directly applied to a wound. The adhesion of the bandage to the wound is promoted by blood from the wound and can be further reinforced by wetting the bandage with an aqueous solution such as water or commercial hand sanitizer gel.

Without wishing to be bound to any particular theory, the turmeric powder is believed to assist in hemostasis and accelerated wound healing. The biocompatible polymer is used to produce an adherent composite which seals the wound and arrests hemorrhage on the spot and, in the bandage embodiment, to confer the mechanical properties and integrity when used to patch wounds.

The resulting composite is useful for the treatment of wounds, radiation induced tissue damage, diabetic ulcers, sealing wounds post tumor removal for healing and elimination of resident cancerous cells at tumor margins and other skin and diseased conditions. Sealing and healing of traumatic wounds without the need for stitches and can be used on the battlefield, by emergency responders, ambulance staff and by the public at all locations to prevent bleeding including situations such as public shootings. The disclosed composite is also useful for treating splanchic and junctional wounds.

Turmeric powder is the dried powdered rhizomes of *Curcuma longa* of the ginger family. Turmeric powder comprises 60-70% carbohydrates, 6-13% water, 6-8% protein, 5-10% fat, 3-7% dietary minerals, 3-7% essential oils such as turmerone and germacrone, 2-7% dietary fiber, and 1-6% curcuminoids. (including curcumin). Importantly, the use of curcumin alone was not found to promote blood clotting, rather it does the reverse. It is a well-known anticoagulant (Kim D C, Ku S K, Bae J S. Anticoagulant activities of curcumin and its derivative. BMB Rep. 2012 April; 45(4):221-6. doi: 10.5483/bmbrep.2012.45.4.221. PMID: 22531131). The turmeric powder may be passed through a 100 mesh (149 micron) sieve such that the resulting particles are smaller than 149 microns in diameter. Generally, turmeric powder is present in the suspension at a concentration between 0.1 g per mL and 2 g per ml. In one embodiment, the concentration is between 0.1 g per mL and 1 g per mL. In yet another embodiment, the concentration is between 0.1 g per mL and 0.5 g per mL.

Traditionally, medical fibers and sutures are prepared by electrospinning. However, these techniques require the bioactive compound(s) be soluble. Turmeric powder is a complex mixture of multiple components, each of which has its own solubility characteristics Some of the components of turmeric powder are water soluble, others are water insoluble while still others are soluble but only to a limited degree. That makes turmeric powder an extraordinarily difficult candidate to incorporate into a nanofiber mat or commercial hemorrhage treatment.

A variety of biocompatible polymers may be used. Polymers include, but not limited to, (X:Y) poly(DL-lactide-glycolide) (PLGA) where X and Y percentage of the two monomers present in the final polymer. The values of X and Y can vary between 0-100% (to vary the inherent viscosity of the polymer between 0.1-1.75 dL per g) and include including linear and branched polymers. Examples include poly(lactide-co-glycolide) 50:50 (PLGA 50:50); poly(lactide-co-glycolide) 75:25 (PLGA 75:25); poly(lactide-co-glycolide) 25:75 (PLGA 25:75); and poly(D,L) lactide (PDLLA). In one embodiment, PLGA is used as it is biocompatible, biodegradable, bioresorbable and approved by the U.S. Food and Drug Administration (FDA) for various applications including sutures. Other biocompatible polymers include poly(glycolide co-caprolactone) (PCL), polyvinyl alcohol, polydioxanone, poly(trimethylene carbonate), catgut, silk, gelatin, collagen, extracellular matrix proteins. Nylon, polyester, polyvinylidene fluoride (PVDF), polypropylene, and ultra-high molecular weight polyethylene (UHMWPE), polytetrafluoroethylene and cyanoacrylate-based polymers.

Likewise, a variety of volatile organic solvents may be used. Examples includes, but are not limited to, acetone, methyl ethyl ketone, ethanol, diethyl ether and other volatile ethers, isopropanol and other short chain alcohols, water, aqueous solutions with added salts including buffered solutions, acetonitrile, hexafluoroisopropanol and mixtures of these solvents.

Antibiotics may also be added to the formulation. Examples of suitable antibiotics include silver nanoparticles and triclosan.

Figure 1B:
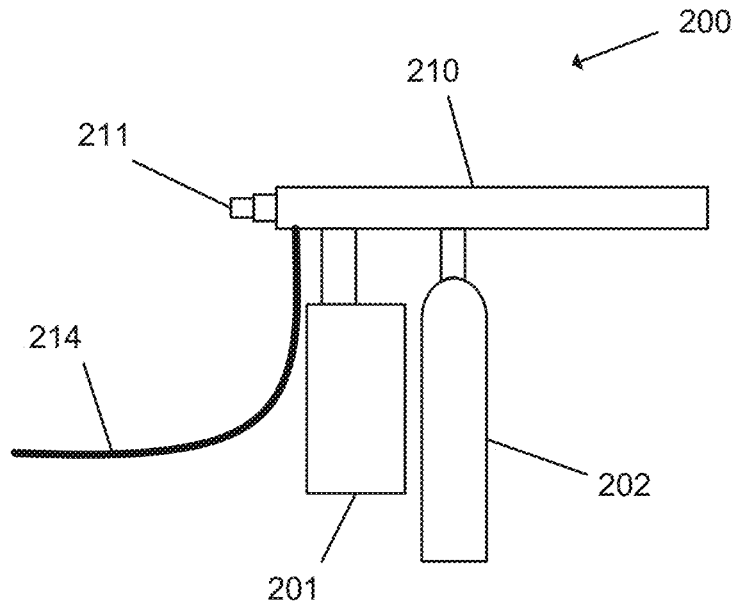

Suitable spraying devices include, but are not limited to, aerosol cans commonly used to dispense spray paints, bottom and top loading airbrushes and compressed air powder dispensers such as those used in fire extinguishers. The pressurized gas used to power the airbrush include but are not limited to compressed air, carbon dioxide, nitrogen. In one embodiment, the spraying device uses a spraying needle with an orifice of at least 0.5 mm to prevent clogging. FIG. 1A depicts one example of a spraying device 100. A compressed gas cylinder 102 connected to a gas regulator 104. The compressed gas cylinder 102 may be, for example, a carbon dioxide compressed gas cylinder. A quick-release connector 106 connects to a hose 108 which, in turn, connects to an airbrush 110 via a connector 112, such as a brass screw fitting. The airbrush 110 has a top loading container 101 that holds the turmeric powder suspension. The airbrush 110 has a top loading container 101 that holds the turmeric powder suspension. FIG. 1B depicts another example of a spraying device 200. Device 200 comprises a comprised gas cylinder 202 connected directly to an airbrush 210. The turmeric powder suspension is stored in bottom loading container 201. When the airbrush 210 is actuated, the turmeric powder suspension is deployed through a nozzle 211 of the airbrush 210. In some embodiments an extendable wand 214 is present to assist in maintaining a desired distance from the target area. For example, the extendable wand 214 may be extended to a distance of 20 cm. The tip of the extendable wand 214 is then placed proximate the wound or other target area, thereby maintaining a distance of 20 cm from the wound.

Exemplary Embodiment

A 20 oz. $CO_2$ bottle (Power tank. CYL-2140-MBK) was attached to a $CO_2$ flow regulator from the same company (REG-4012C) and connected to a Master Hi-Flow S622 Pro Set Dual-Action Siphon Feed Airbrush Set with Nozzle (0.8 mm) and Bottle (From TCP Global Inc.) using a high pressure braided, 5,000 PSI, hose (HSE-1241i) and coupler. The cylinder purchased is used for paint ball, the airbrush for painting and other art related applications. The regulator and connector used to assemble the portable device described herein were assembled based the design of the portable device shown in FIG. 1A.

Because the carbon dioxide cylinder was connected to the regulator with an industrial quick release connector, it afforded rapid assembly and disassembly of the unit. The apparatus used the minimum number of connections as well as only a single moving part, the airbrush gun trigger. The number of connections as well the moving points were reduced in this robust design.

100 mg of pure PLGA (PLGA 50:50 ester terminated viscosity of (0.7-0.9) from Sigma or Evonik corporation or Polysciences Inc.) and 1 mL HPLC grade acetone was combined to produce a 9% (m/v) PLGA solution. The 1 mL of PLGA solution was mixed thoroughly with 0.3 g of turmeric powder. Commercial turmeric powder sieved using a 100 mesh sieve was employed for the studies. The $CO_2$ cylinder was opened to let the gas flow to the airbrush. The gas was regulated to release at a pressure 60 psi. The PLGA and turmeric powder were placed into the solvent receptacle of the airbrush. Two types of airbrushes were tested: a siphon fed bottom loading airbrush S622 and a top loading gravity fed airbrush G 22 (both from TCP Global Inc.). For the gravity feed airbrush, the PLGA and turmeric solution were placed into the barrel in 0.5 mL increments, in order to reduce clogging. A siphon feed S622 feed airbrush with a needle size of 0.8 mm was used. The needle diameter of 0.8 mm is much larger than the turmeric particles overcoming any possibility of clogging and settling of the turmeric suspension. The $CO_2$ pressure could be varied between 20-80 psi. The PLGA concentration varied between 3-9%. The turmeric powder concentration between the range of 0.1-1 g per ml and the distance of the target area from the tip of the airbrush from 5-50 cm. In one embodiment 60 psi of $CO_2$ is used to power the SS622 airbrush. The mats (both control PLGA and turmeric PLGA) were directly produced on a target surface which was either a bleeding wound or a sterile surface such as a glass slide when it is placed 20 cm away from the nozzle of the airbrush.

Due to the biocompatible nature of the composite, the composite can remain on the wound for a prolonged period of time. In one embodiment, the composite is left on the wound for a period of at least 8 hours. In another embodiment, the composite is left on the wound for a period of at least 24 hours. In another embodiment, the composite is left on the wound for a period of at least 48 hours. In another embodiment, the composite left on the wound for a period of at least 72 hours. In still another embodiment the composite is left undisturbed in wounds such a deep knife wound until the wound healing is complete and the composite is absorbed by the body.

Wound Closure Example

Figure 2A:
FIG. 2A depicts a mouse with a wound that is being treated with a turmeric powder mat formed in accordance with this disclosure.
Figure 2B:
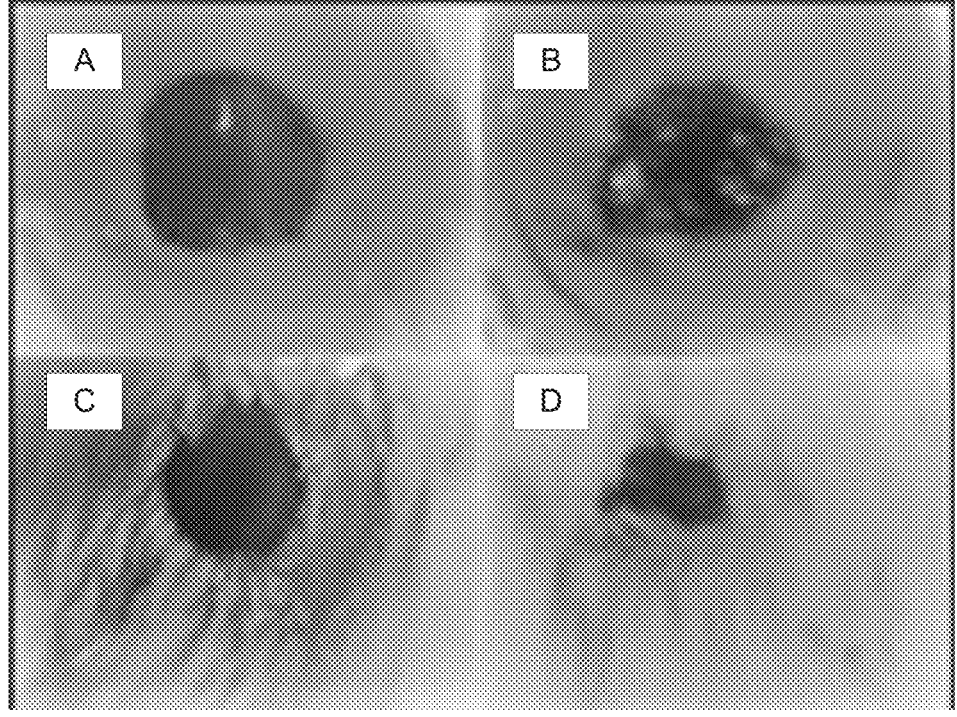
FIG. 2B depicts two wounds after five days of healing wherein panel A (before) and panel B (after five days) depict a control and panels C and D show a wound before treatment with the disclosed composite (panel C) and after five days (panel D).

Referring to FIG. 2A, full thickness skin wounds of 1 cm diameter were made in the thoracic region of CD-1 mice. A premade turmeric-nanocomposite bandage was moistened which caused it to be securely adhered to the wound surface. Referring to FIG. 2B, the healing of the wound was accelerated in the case of the turmeric-PLGA mat (0.3 turmeric powder per mL of a 9% (m/v) solution of PLGA (50:50) in acetone) (panel C day 1 and panel D day 5) when compared to a control PLGA mat (zero turmeric powder in a 9% (m/v) solution of PLGA (50:50) in acetone) (panel A day 1 and panel B day 5) when observed five days after application. Significant contraction in the wound size can be seen by day 5 (FIG. 2B, panel D) for the turmeric power-PLGA mat treated animal.

Hemorrhage Arrest Experiment:

A mouse tail was amputated 2 cm from tip. After amputation (10 seconds) the bleeding tail was treated with turmeric powder (0.3 g per mL) in 9% (m/v) solution of PLGA (50:50) in acetone dispensed from an airbrush device. The turmeric composite was formed in real time on the bleeding tail and arrested hemorrhage instantly. The bleeding tail was 20 cm distance from the airbrush nozzle which is the optimum distance at which the composite is formed.

Mat Example

A mat of the composite material was created from the airbrush by actuating an airbrush to dispense the suspension on a glass microscopic slide. Other suitable surfaces may also be used provided the adhesion between the composite and the surface is relatively low. The standard conditions were 60 PSI pressure and placing the target glass slide at 20 cm from the airbrush nozzle ensures that the final mat is essentially free of solvent and can be readily the peeled from the surface and formed into a roll.

Figure 3A:
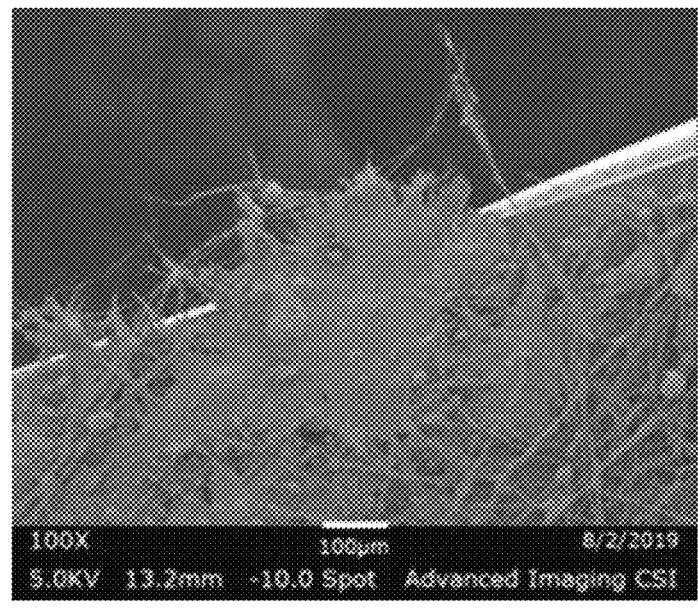
FIG. 3A and FIG. 3B are two scanning electron microscope (SEM) images of a composite made according to this disclosure.
Figure 3B:
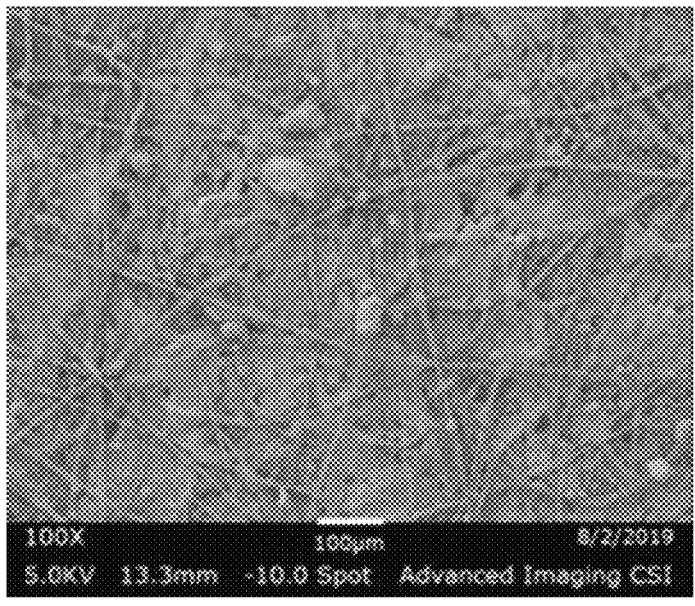

FIG. 3A and FIG. 3B depict the results of scanning electron microscopy (SEM) in order to classify the morphology of the mat. The nanomat was sputter coated with a 10 nm coating of Au-PD on a glass microscope slide. The glass microscope slide was fixed to an aluminum SEM stub. The fibers were imaged at an accelerating voltage of 5 kilovolts and at a magnification of 100× on an AMRAY 1910 field emission scanning electron microscope. The resulting images show the web like formation of the nanofiber mat. SEM images of (0.3 g per mL) turmeric PLGA nanofibers were produced by solution blow spinning using the standardized conditions of 60 psi and mat production on a glass slide placed 20 cm from the nozzle of the airbrush. The images were taken at 5.0 kV and 100× magnification.

Fluid Pressure

Advantageously, the composite is water impermeable and resistant to the high pressure the heart exerts upon the arterial walls. This ensures the composite is useful to stop arterial bleeding despite the fluid pressure of the escaping blood. To simulate these conditions 4 mL of 10% (m/v) PLGA/acetone solution with turmeric powder (0.3 g per mL) was sprayed onto the mouth (mouth diameter 2 cm) of a plastic bottle filled with 280 mL of deionized water the distance of the airbrush nozzle from the mouth of the bottle being 20 cm. Using the mass of the water and the area of the bottle mouth, the exerted pressure was calculated as equal to 65 mmHg which is equivalent to normal arterial pressure. Upon inversion, the water contained within the bottle did not penetrate the membrane, and the membrane itself did not rupture. This demonstrates the efficacy of turmeric-PLGA nanofibers for sealing of arteries.

Advantages:

The disclosed composition has numerous advantages. Unlike other bandages, contact with water enhances the adhesion of the disclosed composite. This has been tested using the composite on mice wounds and skin. An additional case study was performed on a puncture wound on a human finger which was treated with the turmeric-PLGA bioactive bandage also showed enhanced adhesion upon contact with water. Additionally, the painful process of removing and replacing the commercial bandages, which also significantly disrupts wounds healing, is avoided with the disclosed composition. Instead, the same piece initially applied will continue to serve as a wound healing agent over several days. The airbrush device with turmeric-PLGA solution is ideal for coating a large surface area such as a large glass sheet or other sheets of large surface area (e.g. 3 foot by 3 foot). The composite maybe be directly applied in situations of injury that remove a large area of skin (e.g. burns) by just placing the composite on the area to be treated and wetting it with any commercial hand sanitizer.

The application method also permits a user to apply the composite without contacting blood which could potentially be contaminated. In one embodiment, a distance of at least 10 cm is maintained between the spraying device and the wound during the application. In another embodiment, a distance of at least 20 cm is maintained.

At least one of the active ingredients in turmeric powder (curcumin) has moderate anti-cancer activity. Leaching studies confirmed that a concentration of curcumin higher than 20 micro molar (higher than the IC50 of curcumin for most cancer cell lines) is released over a period of weeks from 0.3 g per ml curcumin in 9% PLGA nanomats. The IC50 of 20 micromolar for curcumin can be verified from peer reviewed literature.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A method for treating a wound, the method comprising:
    spraying a bleeding wound with a composition of matter comprising:
        a volatile organic solvent that at least partially evaporates during the spraying;
        a biocompatible polymer;
        turmeric powder; and
    permitting the volatile organic solvent to evaporate, thereby forming a hemostatic composite on the bleeding wound, wherein the hemostatic composite stops the bleeding.

2. The method as recited in claim 1, further comprising leaving the hemostatic composite on the bleeding wound for a period of at least 8 hours.

3. The method as recited in claim 1, wherein the biocompatible polymer is poly (lactic-co-glycolic acid) (PLGA).

4. The method as recited in claim 1, wherein the composition of matter further comprises an antibiotic.

5. The method as recited in claim 1, wherein the composition of matter further comprises silver nanoparticles.

6. The method as recited in claim 1, wherein the composition of matter consists of the volatile organic solvent, the biocompatible polymer and the turmeric powder.

7. The method as recited in claim 6, wherein the biocompatible polymer is poly (lactic-co-glycolic acid) (PLGA).

8. The method as recited in claim 7, wherein the volatile organic solvent is acetone.

9. The method as recited in claim 1, wherein the spraying is performed by a spraying device and a distance of at least 10 cm is maintained between the spraying device and the bleeding wound during the step of spraying.

10. A method for treating a wound, the method comprising:
    spraying a bleeding wound with a composition of matter comprising:
        a volatile organic solvent that at least partially evaporates during the spraying;
        a biocompatible polymer;
        turmeric powder; and
    permitting the volatile organic solvent to evaporate, thereby forming a hemostatic composite on the bleeding wound, wherein the hemostatic composite stops the bleeding; wherein the bleeding wound is an arterial wound with arterial bleeding and the hemostatic composite stops the arterial bleeding on contact.

11. The method as recited in claim 1, where the bleeding wound is a splanchnic or junctional wound.

12. The method as recited in claim 1, wherein the spraying occurs using a spraying device comprising an airbrush having a spraying needle with an orifice of at least 0.5 mm.

13. The method as recited in claim 1, wherein the method further comprises applying an aqueous solution to the hemostatic composite.

14. A method for treating a wound, the method comprising:
    spraying a bleeding wound with a composition of matter comprising:
        a volatile organic solvent that at least partially evaporates during the spraying, the volatile organic solvent selected from the group consisting of acetone, ethanol and isopropanol;
        a biocompatible polymer present at a concentration of 10% (m/v) relative to the volatile organic solvent;
        turmeric powder; and
    permitting the volatile organic solvent to evaporate, thereby forming a hemostatic composite on the bleeding wound, wherein the hemostatic composite stops the bleeding.

15. The method as recited in claim 10, wherein the biocompatible polymer is poly (lactic-co-glycolic acid) (PLGA).

16. The method as recited in claim 10, wherein the composition of matter further comprises an antibiotic.

17. The method as recited in claim 10, wherein the composition of matter consists of the volatile organic solvent, the biocompatible polymer and the turmeric powder.

18. The method as recited in claim 17, wherein the biocompatible polymer is poly (lactic-co-glycolic acid) (PLGA).

19. The method as recited in claim 18, wherein the volatile organic solvent is acetone.

* * * * *